(12) United States Patent
Brill et al.

(10) Patent No.: US 10,347,373 B2
(45) Date of Patent: Jul. 9, 2019

(54) INTELLIGENT INTEGRATION, ANALYSIS, AND PRESENTATION OF NOTIFICATIONS IN MOBILE HEALTH SYSTEMS

(71) Applicant: Voalte, Inc., Sarasota, FL (US)

(72) Inventors: Eric Brill, Jensen Beach, FL (US); Philip N. Fibiger, Winter Park, FL (US)

(73) Assignee: Voalte, Inc., Sarasota, FL (US)

( * ) Notice: Subject to any disclaimer, the term of this patent is extended or adjusted under 35 U.S.C. 154(b) by 0 days.

(21) Appl. No.: 15/647,216

(22) Filed: Jul. 11, 2017

(65) Prior Publication Data

US 2017/0308650 A1    Oct. 26, 2017

Related U.S. Application Data

(63) Continuation-in-part of application No. 14/485,760, filed on Sep. 14, 2014, now Pat. No. 9,734,301.

(51) Int. Cl.

| | |
|---|---|
| G16H 10/60 | (2018.01) |
| G16H 15/00 | (2018.01) |
| G16H 50/20 | (2018.01) |
| G16H 50/50 | (2018.01) |
| G16H 40/63 | (2018.01) |
| G06F 19/00 | (2018.01) |
| G08B 25/00 | (2006.01) |

(52) U.S. Cl.
CPC ............. *G16H 10/60* (2018.01); *G16H 15/00* (2018.01); *G16H 40/63* (2018.01); *G16H 50/20* (2018.01); *G16H 50/50* (2018.01); *G06F 19/3418* (2013.01); *G08B 25/001* (2013.01)

(58) Field of Classification Search
CPC ........ G16H 10/60; G16H 40/63; G16H 50/50; G16H 50/20; G16H 15/00; G08B 25/001; G06F 19/3418
See application file for complete search history.

(56) References Cited

U.S. PATENT DOCUMENTS

| | | | | |
|---|---|---|---|---|
| 7,671,733 | B2 * | 3/2010 | McNeal | A61B 5/0002 340/539.12 |
| 9,129,501 | B1 * | 9/2015 | King | G08B 29/02 |
| 9,764,082 | B2 * | 9/2017 | Day | A61M 5/142 |
| 9,971,871 | B2 * | 5/2018 | Arrizza | G06F 8/65 |

(Continued)

*Primary Examiner* — Fekadeselassie Girma
(74) *Attorney, Agent, or Firm* — Long Technology Law, LLC; Joseph L. Long

(57) ABSTRACT

Systems and methods can support managing clinical alerts presented to clinical care users. An integration management system can maintain models of clinical alert events in the context of user behaviors and in the context of patients. Alarm indications associated with the patient may be received along with context information associated with the patient. Patient information may be received from an electronic medical record system. Integrated decision processing can integrate two or more of the alarm indication, the models of clinical alert events, the patient context, and the information from the electronic medical record system. The integrated decision processing can determine if a clinical alert is to be generated, what type, and to whom. The clinical alert can be transmitted to a target user. A response can be received and interpreted. Information associated with the patient may be updated into the electronic medical record system.

20 Claims, 5 Drawing Sheets

(56) References Cited

U.S. PATENT DOCUMENTS

| | | | | |
|---|---|---|---|---|
| 10,042,986 B2* | 8/2018 | Ruchti | | G06F 19/3468 |
| 10,061,899 B2* | 8/2018 | Miller | | A61M 1/288 |
| 10,238,799 B2* | 3/2019 | Kohlbrecher | | A61M 5/142 |
| 10,238,801 B2* | 3/2019 | Wehba | | G16H 50/20 |
| 10,242,060 B2* | 3/2019 | Butler | | G06Q 10/06 |
| 10,248,856 B2* | 4/2019 | Moore | | G06K 9/00442 |
| 2004/0183684 A1* | 9/2004 | Callaway | | G08B 21/02 |
| | | | | 340/573.1 |
| 2005/0146430 A1* | 7/2005 | Patrick | | G08B 19/005 |
| | | | | 340/531 |
| 2005/0242928 A1* | 11/2005 | Kirkeby | | G08B 5/22 |
| | | | | 340/286.07 |
| 2007/0153993 A1* | 7/2007 | Cohen | | H04M 11/002 |
| | | | | 379/100.05 |
| 2007/0192133 A1* | 8/2007 | Morgan | | G06F 19/321 |
| | | | | 705/2 |
| 2008/0033752 A1* | 2/2008 | Rodgers | | G06Q 10/109 |
| | | | | 705/2 |
| 2011/0009715 A1* | 1/2011 | O'Reilly | | G06F 19/3456 |
| | | | | 600/302 |
| 2011/0202495 A1* | 8/2011 | Gawlick | | A61B 5/0002 |
| | | | | 706/59 |
| 2012/0169467 A1* | 7/2012 | Condra | | G06F 19/3418 |
| | | | | 340/8.1 |
| 2012/0316897 A1* | 12/2012 | Hanina | | G06F 19/3456 |
| | | | | 705/3 |
| 2013/0085771 A1* | 4/2013 | Ghanbari | | G16H 10/60 |
| | | | | 705/2 |
| 2013/0214925 A1* | 8/2013 | Weiss | | G08B 25/001 |
| | | | | 340/539.11 |
| 2014/0132413 A1* | 5/2014 | Fox | | A61B 5/0022 |
| | | | | 340/573.1 |
| 2015/0099946 A1* | 4/2015 | Sahin | | A61B 5/16 |
| | | | | 600/301 |
| 2017/0235910 A1* | 8/2017 | Cantillon | | G06F 19/3418 |
| | | | | 705/2 |
| 2017/0235912 A1* | 8/2017 | Moturu | | G06F 19/3418 |
| | | | | 705/2 |
| 2017/0357756 A1* | 12/2017 | Fidone | | G06F 19/328 |
| 2018/0032879 A1* | 2/2018 | De | | G06N 5/022 |
| 2018/0060494 A1* | 3/2018 | Dias | | G06F 19/325 |

* cited by examiner

INTELLIGENT INTEGRATION, ANALYSIS, AND PRESENTATION OF NOTIFICATIONS IN MOBILE HEALTH SYSTEMS

CROSS-REFERENCE TO RELATED APPLICATIONS

This application is a Continuation-in-Part of application Ser. No. 14/485,760 filed on Sep. 14, 2014, and entitled "Intelligent Presentation of Alarms and Messages in Mobile Health Systems." The complete disclosure of the above-identified parent application is hereby fully incorporated herein by reference.

BACKGROUND

Various instruments and events within a healthcare enterprise can generate alarms for notifying point-of-care staff such as nurses and physicians of events and conditions regarding patients. Electronic Medical Record systems maintain an increasing portion of patient related information, but generally operate in isolation from other electronic systems within the healthcare enterprise.

Notifications associated with alarms and other relevant clinical information generally are not automatically provided to the correct staff member. They are also generally not presented in the manner that most efficiently improves care provisioning and ultimately patient outcomes. These challenges are often complicated by patient turnover, changes in patient status, staff assignment updates, or staff modifications due to shift changes.

The enormous quantities of ever-shifting information regarding personnel, patients, and events within a healthcare facility complicate routing updates to the most proximate, available, or appropriately skilled staff member and presenting it in the most efficient manner. Traditionally, much of this information is managed and communicated using paper, clipboards, white boards, files, charts, fax machines, and other manual methods that are slow, inefficient, non-ubiquitous, and error-prone.

As more systems in the healthcare enterprise have become computerized and networked, electronic alarms have become more numerous and frequent. As clinicians become desensitized to frequent interruptions of these alarms, they often begin to ignore the alarms or even turn them off. This phenomenon is referred to as alarm fatigue.

There is a need in the art for healthcare enterprise notification technologies that can intelligently integrate, analyze, predict, and present a broad spectrum of information regarding personnel, patients, and events such that notifications and presented information improve patient outcomes and reduce costs.

SUMMARY

In certain example embodiments described herein, methods and systems can support managing clinical alerts presented to clinical care users. An integration management system can maintain models of clinical alert events in the context of user behaviors and in the context of patients. Alarm indications associated with the patient may be received along with context information associated with the patient. Patient information may be received from an electronic medical record system. Integrated decision processing can integrate two or more of the alarm indication, the models of clinical alert events, the patient context, and the information from the electronic medical record system. The integrated decision processing can determine if a clinical alert is to be generated, what type, and to whom. The clinical alert can be transmitted to a target user. A response can be received and interpreted. Information associated with the patient may be updated into the electronic medical record system.

These and other aspects, objects, features, and advantages of the example embodiments will become apparent to those having ordinary skill in the art upon consideration of the following detailed description of illustrated example embodiments.

DETAILED DESCRIPTION OF EXAMPLE EMBODIMENTS

Overview

The technology presented herein can significantly improve the efficacy of various alarms, messages, and notifications within a healthcare enterprise to improve patient outcomes and reduce costs. The technology can leverage machine intelligence to collect, aggregate, evaluate, process, and model data to enable the intelligent presentation and acknowledgement of alarms, events, alerts, and messages between various combinations of caregivers, instrumentation, and information systems. The machine intelligence can extend to modeling, predicting, and optimizing behaviors of users as individuals or according to various roles and/or assignments. Application of this technology can reduce alarm fatigue while improving the delivery and routing of notifications associated with alarms. Acknowledgment or response to these notifications may also be improved through the application of the technology presented herein.

The functionality of the various example embodiments will be explained in more detail in the following description, read in conjunction with the figures illustrating the program flow. Turning now to the drawings, in which like numerals indicate like (but not necessarily identical) elements throughout the figures, example embodiments are described in detail.

Example System Architectures

Figure 1:
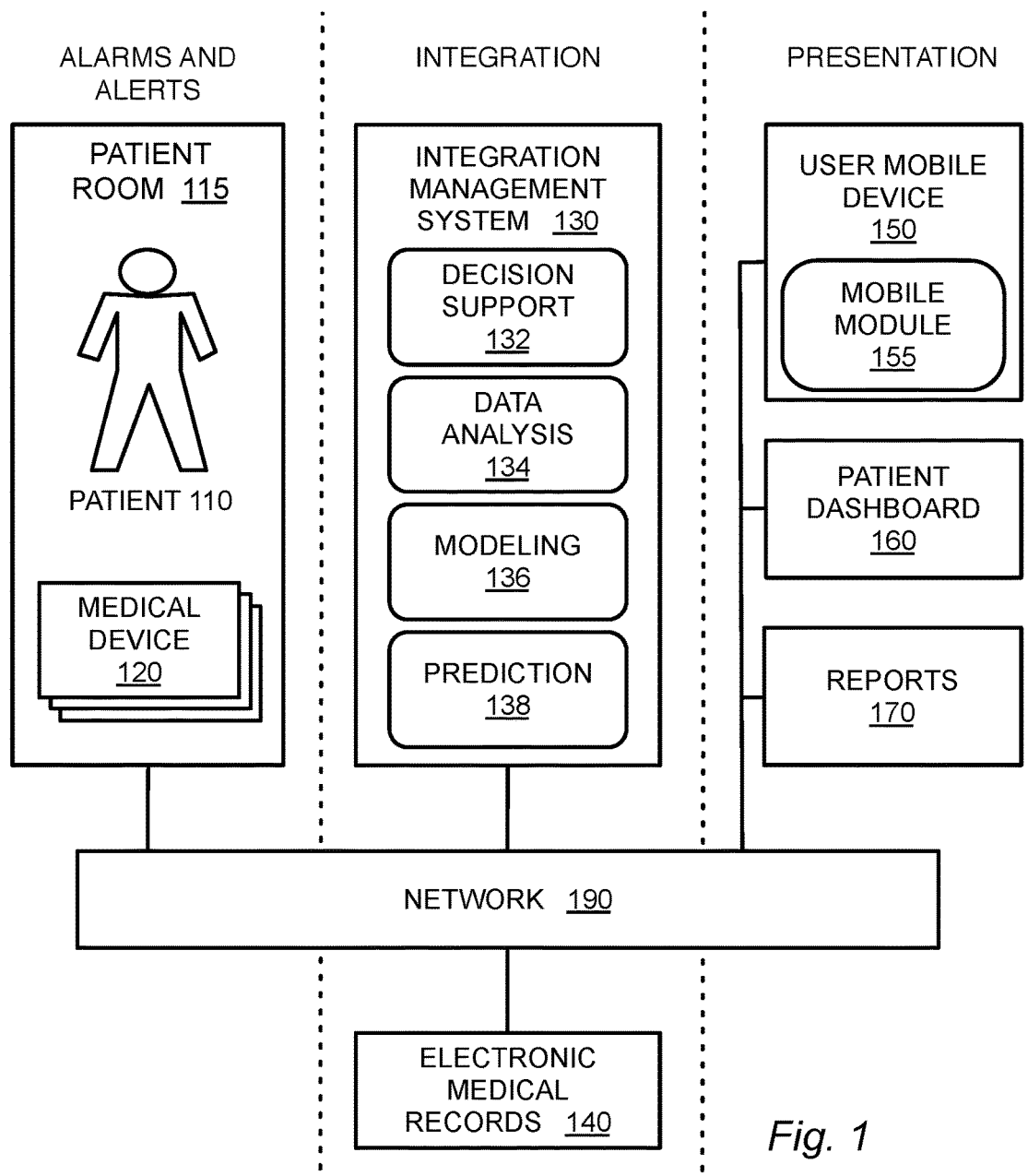
FIG. 1 is a block diagram depicting an integration management system within a healthcare enterprise in accordance with one or more embodiments presented herein.

FIG. 1 is a block diagram depicting an integration management system 130 within a healthcare enterprise in accordance with one or more embodiments presented herein. The integration management system 130 can execute one or more modules for decision support 132, data analysis 134, modeling 136, and prediction 138. These operations can integrate and process alarms and alerts along with information from electronic medical records 140 associated with a patient 110. The alarms may originate from medical devices 120 in a patient room 115 or otherwise associated with the patient 110. The integration management system 130 can present information to a user mobile device 150 operable to execute one or more mobile modules 155. The integration management system 130 can also present information to a patient dashboard 160 or in various generated reports 170. The various systems and components associated with the integration management system 130 may be in data communications through one or more networks 190.

A context for operation of the technology presented herein may be considered in three layers, as illustrated. These three layers may be referred to as a layer for alarms and alerts, an integration layer, and a presentation layer. Within the first layer, alarms and alerts may originate from various systems or events associated with the patient 110. These systems may include medical devices 120 in the patient room 115, labs associated with the patient 110, clinical events associated with the patient 110, events related to clinical providers associated with the patient 110, and so forth. Within the second layer, or integration layer, the integration management system 130 can integrate and process alarms and alerts along with information from electronic medical records 140. Within the third layer, or presentation layer, information and results from the integration layer may be presented through various modalities. Examples of such modalities may include interfaces associated with a user mobile device 150, a patient dashboard 160, or various generated reports 170.

The medical devices 120 in the patient room 115 or otherwise associated with the patient 110 may include various monitors or telemetry devices. For example, the medical devices 120 may include heart monitors, respiration monitors, blood pressure monitors, blood oxygen sensors, intravenous delivery systems, pain management systems, fetal monitors, and so forth. The medical devices 120 may also include smart beds that can report patient movement, when the patient exits or enters, when the guardrails have moved, and other such specifics. Similarly, the medical devices 120 may include a call button at the bed or in the restroom, motion sensors, communications devices, and so forth. Any of these, or other such medical devices 120 can generate alarms or alarm indicators for a variety of reasons. Generally, the alarms are generated when a certain condition obtains such as a measurement threshold being exceeded or a sensor or switch being activated.

It should be appreciated that alarms and alerts may be generated by various other sources in addition to the medical devices 120. According to one example, an alert may be generated to indicate that lab work has been completed and results are available. According to another example, an alert may be generated to indicate that it is time for a patient 110 to receive a dose of medication or a session associated with physical therapy, respiratory therapy, or some other treatment or procedure.

The patient room 115 may include communications or monitor devices. These may include a camera, a video display, a microphone, a speaker, or various other sensors. The microphone and speaker can support voice communications or intercom functionality. Addition of a camera and/or video display can support video monitoring or even video conferencing. For example, a staff user can communicate with, listen to, or visually observe the patient 110 from a user mobile device 160 or other computing machine or communication device. For example, the patient may be visually monitored from a computer display at a nurse station. The various communication modalities may be supported by a communication management server (not illustrated here) and may interface through a voice gateway to existing voice communication systems (such as VoIP, PBX, or POTS systems) or similar video conferencing systems. Events associated with these patient communication modalities may also generate alarms and alerts associated with the patient 110.

The integration management system 130, in conjunction with associated modules for decision support 132, data analysis 134, modeling 136, prediction 138, or other related modules may operate to perform functionality presented herein. While traditional middle-wear may have directly presented any generated alarms without evaluation, aggregation, or processing, this functionality may be provided by the integration management system 130. This technology may be referred to as "smart alarms" or "intelligent alarms." It should be appreciated that in addition to the modules for decision support 132, data analysis 134, modeling 136, and prediction 138, the technology presented herein may include or interface with various other modules. It should also be appreciated that any two or more of these modules may be combined into the same module or modules. Furthermore, any one or more of these modules may split functionally, or load share, between two or more modules or execute on two or more computing machines. Any such modules may operate in a parallel, distributed, or networked fashion without departing from the spirit or scope of the technology presented herein. The functionality presented herein may be implemented at the patient room 115, the integration management system 130, the user mobile device 150, some other location within the healthcare enterprises, or in any combination thereof.

Information associated with alarms and alerts may be relayed from their origin (for example, the medical devices 120) to the integration management system 130. Information associated with the patient 110 and various clinical operations within the healthcare enterprise may be communicated between the electronic medical records 140 and the integration management system 130. These communications may leverage various technologies including, for example, Wireless Communications Transfer Protocol (WCTP), Wi-Fi, XML, HTTP, TCP/IP, or various other networking protocols, technologies, or topologies. These communications may follow one or more messaging standards that define how information is packaged and communicated from one system to another. Such standards can specify languages, structures, and/or data types for integrating information between systems. An example of such a standard is Health Level Seven (HL7), which includes a set of rules for information to be shared and processed in a uniform and consistent manner within the healthcare enterprise.

The decision module 132 may process events, such as alarms or alerts, and present resultant notifications to appropriate clinical care providers within a healthcare environment. The decision module 132 may use rule implementation systems, event handlers, or other machine intelligence mechanisms. The decision module 132 can apply rules to presentation of notifications. According to certain example embodiments, where modeling indicates that a particular user is more likely to respond rapidly to an alarm when a particular alert tone is emitted from their user mobile device 150, a rule may be established indicating for the preferred alert tone to be played when an alarm is routed to that user. This rule may be particularly effective when the alarm is critical or when nobody else is available to respond. Various other examples of applying rules for presenting alarms may be implemented according to various embodiments. Rules may also be established for offering alarm response options to users.

The decision module 132 can apply rules for presenting the alarms and alerts to clinical end users. Whether the alarm gets routed, to whom it gets routed, and how it is to be presented may all be determined by applying one or more rules. The rules may be applied according to a rule implementation system associated with the integration management system 130. Application of the rules may leverage various facts or other parameters. These may include information related to the received alarm, context of the clinical users (for example, locations, skills, roles, etc.), context of the patient (for example, from the electronic medical records 140), and relationships between the patient 110 and the clinical users.

The rules may establish how the alarms and alerts might be presented to the clinical users. For example, notifications may be presented as sounds or alarm tones played on the user mobile device 150. Notifications may also be presented as vibrations, flashing lights, graphical display, textual displays, animations, or any combination thereof. Notifications tones may comprise multiple ringtones. Users of the user mobile devices 150 may select alarm tones, or tones may be assigned according to functional criteria. For example, alarm tones may differ according to alert severity. Hands-free alarm presentation may be supported by voice annunciation where information about the alarm is presented at the user mobile device 150 using voice synthesis or recorded voice messages played through a speaker. For example "Attention—Patient Alarm in Room 941." Alarm presentation may evolve over time. For example, if a user does not acknowledge an alarm after a period of time, the volume of the alarm may be increased or the alarm tone or presentation may be altered. The period of time before changing may be preset or may be learned through user modeling. The various styles of presentations as well as specific parameters (how to annunciate voice alarm, what volume to use, to use a tone or vibration, and so on) may be determined and fine-tuned using the behavioral and outcome modeling techniques presented herein. All of these factors may be implemented according to the established rules associated with the integration management system 130.

The integration management system 130 can train the rules according to expected or typical response behavior from the clinical users. The rules can adapt to best manage notification responses according to one or more of various metrics. Example metrics may include how rapidly users acknowledge notifications, reduction in ignored notifications, percentage of notifications that get accepted over rejected, how rapidly or correctly the clinical user addresses the need of the patient 110, user stress reduction, patient health outcomes, patient satisfaction outcomes, cost reductions, readmission reductions, discharge facilitations, and so forth.

The training or adaptation of the rules can support the integration management system 130 in managing notification responses in a fashion that has been learned or adapted by the system to improve user reactions or otherwise assist the user in effectively handing notifications. The training or adaptation of the rules can also support the integration management system 130 in determining when the user is not responded as expected or as they usually do. This determination can serve as a response in itself. For example, if a particular user generally acknowledges alarms within 45 seconds and in a certain instance, 60 seconds have passed without acknowledgement, the integration management system 130 may determine that the user is unavailable. At that time, the integration management system 130 may proceed to forward the alarm to another clinical user, escalate it to a supervisor, or take some other course of action. According to other examples, the integration management system 130 may attempt to use a modified alarm tone after the typical tone was not acknowledged. If the response time of the clinical user, while hearing the modified tone, is less than the user's usual time, then the integration management system 130 may learn to use the modified tone as the primary tone for the user going forward.

According to certain embodiments, the decision support module 132 may make distinctions as to which alarms or alerts should be attended to in a particular order. A triage view may be provided to the clinical users to indicate relative medical urgency.

The data analysis module 134 may use data analysis and data analytic techniques to improve the efficacy of various alarms, messages, and notifications within a healthcare enterprise to improve patient outcomes and reduce costs. Such techniques may include collecting, processing, cleaning, organizing, correlating and learning from various data inputs from any available sources that are relevant. According to certain embodiments, large amounts of data may be collected from electronic medical records 140, alarms, alerts, and various other sources within the healthcare enterprise. Identifying patterns within the collected data can support establishing or refining rules associated with the decision support module 132. Similarly, results of data analysis 134 may influence operations associated with the modeling module 136, or various other machine intelligence or machine learning processes. Applied machine learning techniques may include supervised and/or unsupervised learning.

The modeling module 136 may use data acquired from the data analysis module 134 to create representations of various events. Data modeling may include establishing and analyzing data objects to conceptualize relationships among those data objects. Data modeling can define and analyze data to create frameworks for translating complex systems into recognizable representations of data processes. Data modeling can define data elements and the relationships and structures between them. Data models may evolve in light of new information as it is introduced. The modeling module 136 may build models based on events and correlations to generated outputs given certain combinations of inputs.

The prediction module 138 can attempt to determine events as they are occurring, or before they occur, based on current condition, past events, and established models. Such predicted events may include clinical events within the healthcare enterprise, alarms, alerts, notifications, or other occurrences associated therewith. Predictions may be provided as probability or likelihood of possible events. Models may be leveraged to provide predictions of various outcomes based on incoming data in light of statistical analysis, previous behaviors, or previous actions of objects or individuals. Data prediction may involve risk analysis of various models. According to certain examples, the prediction module 138 may evaluate alarms or alerts associated with a patient 110 along with electronic medical records 140 information related to some number of previous patients and their associated alerts, alarms, and resulting outcomes. The prediction module 138 may establish predicted probabilities of such outcomes for the current patient 110. Thresholds or concerns associated with these predicted outcomes may be appropriately presented to clinical personnel according to the technology presented herein.

Within the third layer, or presentation context, information and results from the integration layer may be presented through various modalities. The integration management system 130 and its associated modules can present various notifications and/or information to clinical care providers. Such presentations may be provided through one or more user mobile devices 150, such as smart phones, tablets, or desktop computers, for example. In addition to these user mobile devices 150, presentations may be provided via the patient dashboard 160 as discussed herein, or generated as reports 170. The user associated with the user mobile device 150 or other presentation mechanism may be a care provider in a hospital or other care facility. The user may be a nurse, physician, therapist, technician, assistant, specialist, or any other care provider. The user can interface with the user mobile device 150 for receiving presentation of, and responding to, various notifications or other messages. The user can receive other information related to the patient 110 via the user mobile device 150. This other information may include voice or video communications, data strips from medical devices 120, and so forth. The mobile modules 155 can provide software, firmware, or hardware for executing the functionality of the user mobile device 150 as discussed herein. Input and output mechanisms associated with the mobile device 150 can include various sensors, input, and output mechanisms. These may include touch screens, microphones, speakers, video displays, and so forth. A location module associated with the mobile device 150 can provide the user mobile device 150 with location awareness for use within the user mobile device 150 or relaying to the integration management system 130. The location module may include GPS, beacon locating, wireless access point positioning, RTLS, or other mapping/location services. Wireless access point positioning can determine the location of the user mobile device 150 based upon which wireless access points it is currently able to connect with and possibly what their respective apparent power levels read as.

It should be appreciated that the user may also interface through a desktop computer or workstation instead of a user mobile device 150. For example, the user may be using a desktop computer system in the office or at a nurse's station in a hospital or other care facility. These systems may be useful for accessing one or more patient dashboards 160, reports 170, or other presentations of information generated with respect to the technology presented herein. It should be appreciated that certain notifications may be directed to health care providers based on roles, assignments, skills, proximity to the patient 110, or various other criteria. These criteria may be specified by rules associated with the integration management system 130.

The patient dashboard 160 may be a presentation device associated with the medical devices 120, and may be physically represented as a television monitor, smart phone, tablet, or some other device capable of displaying visual and/or audible data. The patient dashboard 160 may provide real-time viewable statuses of patients 110. These may include vital signs such as heart rate, blood pressure, or blood sugar levels, for example. The patient dashboard 160 may display or sound alarms and/or alerts associated with medical devices 120. For example, if some measurement of the patient 110 is considered to be outside normal limits, then an alarm or alert may be displayed on one or more patient dashboards 160. Patient dashboards 160 may also provide caregivers with triage views of notifications to separate the notifications by urgency. According to certain embodiments, notifications posted to a patient dashboard 160 that require the most urgency may be presented to one or more user mobile devices 150 as well.

Alert fatigue among care providers may occur when caregivers receive too many alarms, alerts, or notification at their user mobile device 150. The care providers may ignore and/or override the alerts just to stop being interrupted. To help alleviate such alert fatigue, the integration management system 130 may determine when to present notifications to user mobile devices 150 when it is particularly meaningful and not simply annoying. For example, an alert may be presented only when specific attention is necessary from a particular care provider.

Users of the user mobile devices 150 may interface with subscription services associated with the integration management system 130. These services can support subscribing only to notifications meeting certain parameters. For example, notifications associated with skill sets, roles, responsibilities, availability, location, and so forth. By presenting notification to users (for example, via user mobile devices 150) based on these subscription criteria, alarm fatigue can be greatly reduced. Furthermore, healthcare workers may be more productive based on established roles and various other criteria. By receiving only subscribed alarms, a caregiver can be more attentive to their specific role. It should be appreciated that the subscriptions to various events can be manual and/or automated.

The electronic medical records 140 may also be referred to as electronic health records or electronic patient records. Such electronic medical records 140 may be generated and maintained within a healthcare enterprise such as a hospital, integrated delivery network, clinic, or physician office. Electronic medical records 140 can provide patients, physicians, other health care providers, employers, payers, or insurers access to patient medical records. Such access may be provided across multiple facilities. Electronic medical records 140 may be a systematic collection of electronic health information about an individual patient or population. Electronic medical records 140 may include a variety of information such as demographics, medical history, medications, allergies, immunization status, laboratory test results, radiology images, vital signs, personal statistics, age, weight, billing, and insurance information. The electronic medical records system 140 may be implemented to represent data that accurately captures the state of the patient at substantially all times. Patient histories may be viewed from the electronic medical records system 140. Storing the patient information in a single digital system can assist in ensuring data is accurate, appropriate and legible. It can reduce the chances of data replication by providing a singular file that is constantly up to date and obviates any issues with lost forms or paperwork. Electronic medical records system 140 can simplify the extraction of medical data for the examination of possible trends. Thus elucidating long term changes in one particular patient and also simplifying research across populations.

Figure 5:
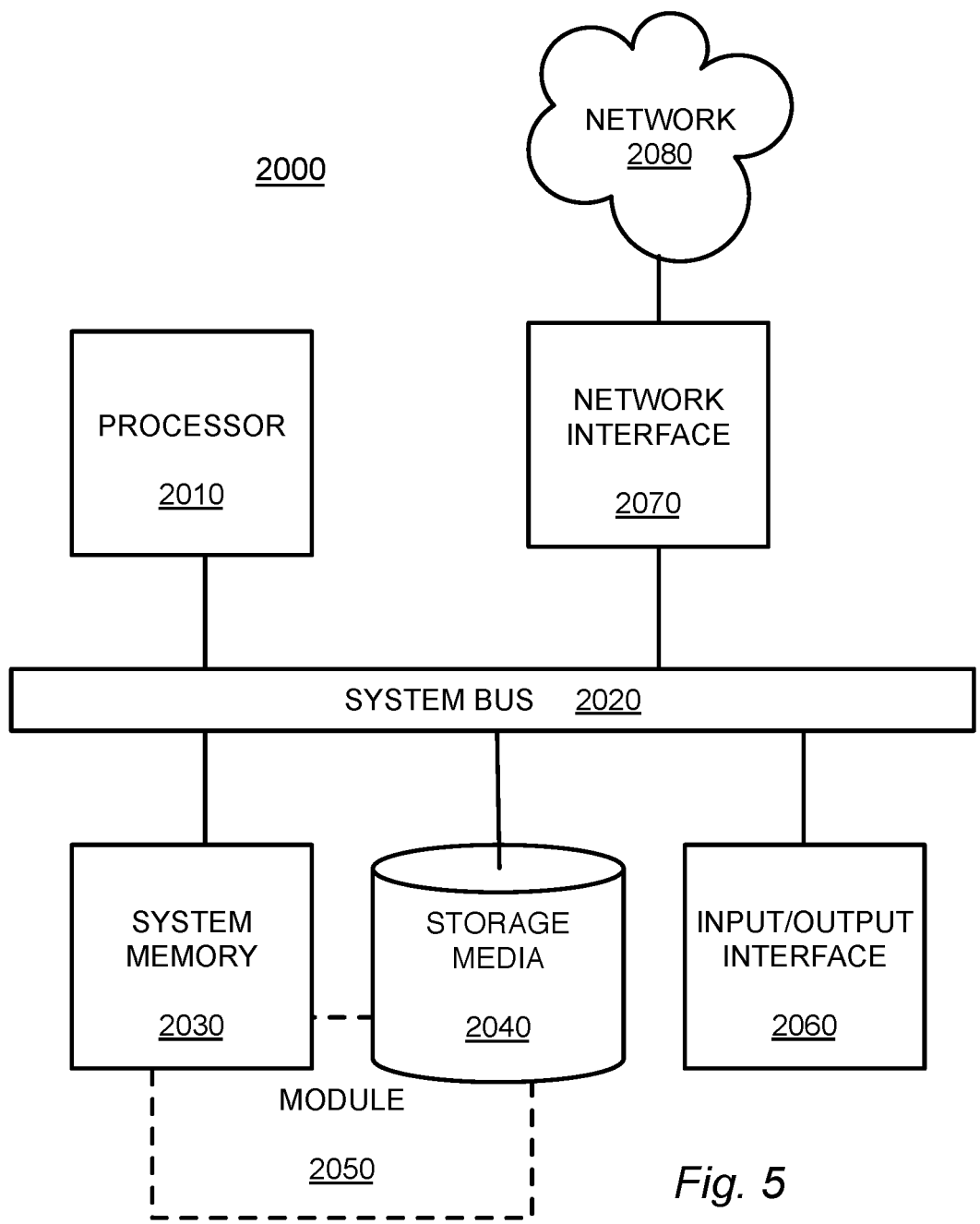
FIG. 5 is a block diagram depicting a computing machine and a module in accordance with one or more embodiments presented herein.

The integration management system 130, user mobile device 150, systems associated with the electronic medical records 140, systems associated with the patient room 115, or any other systems associated with the technology presented herein may be any type of computing machine such as, but not limited to, those discussed in more detail with respect to FIG. 5. Furthermore, any modules (such as the mobile module 155, decision support module 132, data analysis module 134, modeling module 136, or prediction module 138) associated with any of these computing machines or any other modules (scripts, web content, software, firmware, or hardware) associated with the technology presented herein may by any of the modules discussed in more detail with respect to FIG. 5. The computing machines discussed herein may communicate with one another as well as other computer machines or communication systems over one or more networks such as network 190. The network 190 may include any type of data or communications network including any of the network technology discussed with respect to FIG. 5.

Figure 2:
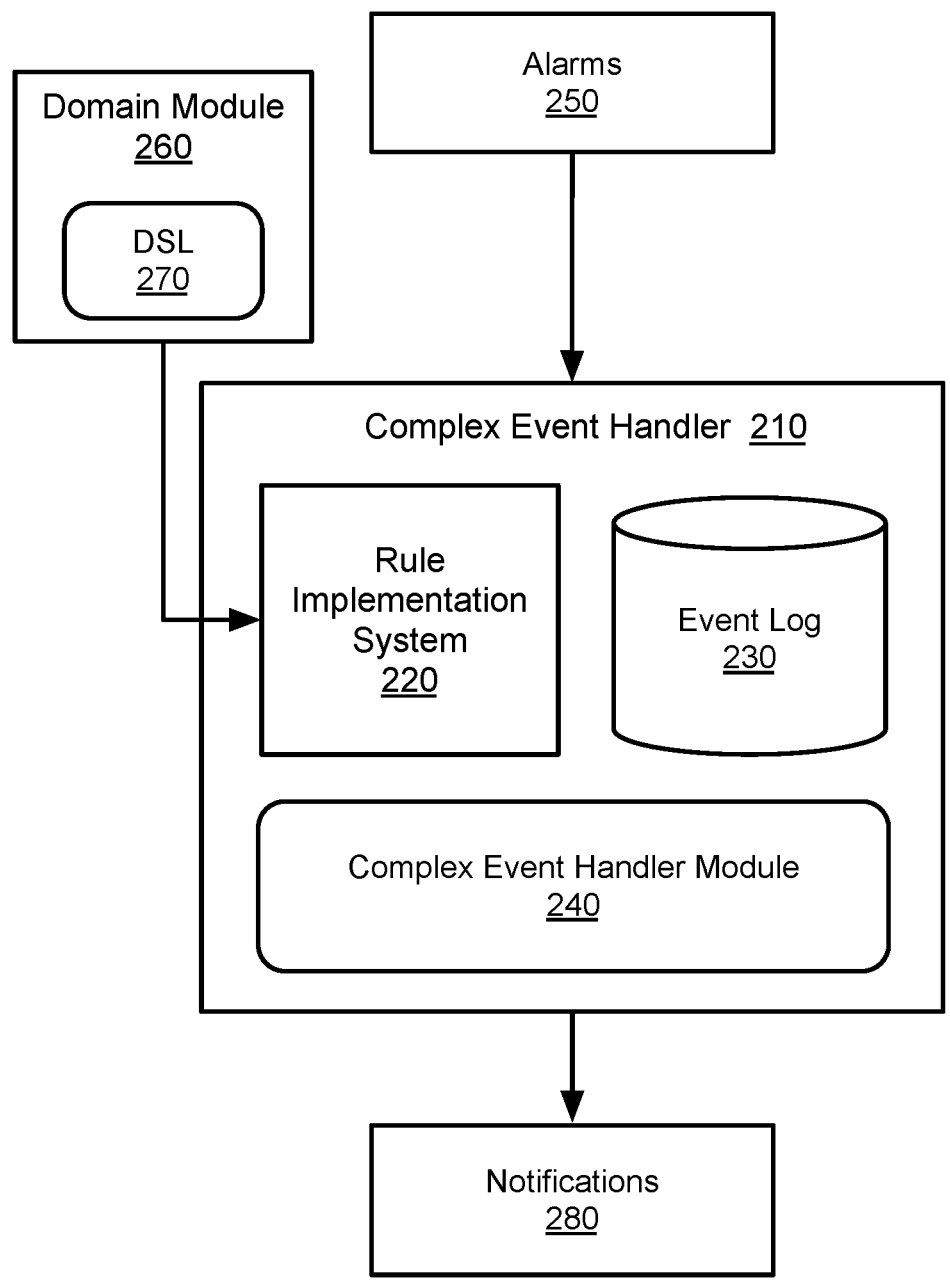
FIG. 2 is a block diagram depicting a complex event handler associated with a rule implementation system and an event log in accordance with one or more embodiments presented herein.

FIG. 2 is a block diagram depicting a complex event handler 210 associated with a rule implementation system 220 and an event log 230 in accordance with one or more embodiments presented herein. The complex event handler 210 can execute in association with a complex event handler module 240. The complex event handler 210 can receive incoming events such as one or more alarms 250. The complex event handler 210 can store incoming events to the event log 230. The complex event handler 210 can match incoming events against rules within the rule implementation system 220. Triggering of the rules within the rule implementation system 220 may also be dependent upon prior events stored in the event log 230. Triggering of rules can generate various actions such as notifications 280. One or more domain modules 260 may provide rules for use within the rule implementation system 220. A domain specific language (DSL) 270 may be used in conjunction with each of the domain modules 260.

The complex event handler 210 can support operations of the integration management system 130 such as those associated with the decision support module 132, data analysis module 134, modeling module 136, or the prediction module 138.

The complex event handler 210 and associated complex event handler module 240 can receive incoming events such as one or more alarms 250. The complex event handler 210 can support making decisions based one or more incoming current events in combination with one or more prior events. The decisions may be determined by the rule implementation system 220 based upon incoming events along with prior events stored within the event log 230.

In addition to the rule implementation system 220 triggering rules based upon incoming events, rules associated with the complex event handler 210 may further depend upon prior events retrieved form the event log 230. The condition of such a rule may be a function of both current incoming events as well as prior events.

According to one or more examples related to an enterprise messaging system, a current event may be generated when user Adam sends a first message to user Beth, both within the same organization. The complex event handler 210 may store, within the event log 230, an event indicating that the first message was sent. Subsequently, user Beth's role within the organization may change. For example, Beth may have been in charge of deliveries on the day when the first message was sent, but is now in charge of customer service. The change in Beth's role may generate an event that may be stored by the complex event handler 210 into the event log 230. At a future point, user Adam may send a second message to user Beth. Sending the message may generate an event, which is received by the complex event handler 210. The complex event handler 210 may trigger a rule within the rule implementation system 220. The complex rule may be a function of both the incoming event (a second message was sent) and two prior events (a first message was sent and the role associated with the receiver has changed). The two prior events may be retrieved from the event log 230 by the rule implementation system 220 while testing the rule. The rule may indicate that if user Adam sends a first message to user Beth, user Beth's role changes, and then user Adam sends a second message to user Beth, one or more actions should alert one or both of the users Adam and Beth to these details. For example, the rule implementation system 220 may generate an action to notify user Adam that user Beth has changed roles within the organization since their last interaction. The rule implementation system 220 may also generate an action to notify user Beth that user Adam sent a message and has been notified of Beth's new role. User Beth may also be provided the opportunity to redirect the second message to the new person in her prior role, if appropriate. Furthermore, user Beth may be provided with an option to ignore the message or to simply continue the conversation with user Adam.

It should be appreciated that rules associated with the complex event handler 210 can act on multiple incoming current events from multiple sources as well as depending upon multiple prior events retrieved from the event log 230. A rule may be a function of any number of incoming current events and any number of prior events.

The rule implementation system 220 may be an example of a rule engine system, production system, or production rule system. These are often used in artificial intelligence, automated planning, expert systems, action selection systems, or other such machine-based knowledge or decision systems.

The rule implementation system 220 may implement a plurality of rules. Each rule may contain a condition that when matched triggers a resultant action. The rule implementation system 220 may receive events that can be pattern-matched against the rule conditions. When a rule condition is properly matched to incoming events and/or stored prior events, the rule action associated with the condition may be triggered. The rule condition may be specifically formatted to match the formatting of the event data associated with incoming events and/or prior events stored within the event log 230. According to various embodiments, the rule implementation system 220 may be based upon a graph database.

The event log 230 may store one or more events received by the complex event handler 210. The event log 230 can store events within a computerized database, a computer memory, a computer data storage system, a cloud-based data store, any other data storage mechanisms, or any combinations thereof. Events may be time-stamped and/or date-stamped in order to establish when the complex event handler 210 received respective events. According to various embodiments, stored prior events may be removed from the event log 230 when they reach a specified expiration date. Similarly, a rule may trigger indicating removal of the event entry from the event log 230. A given rule may also indicate a specified time window of prior events to be considered when evaluating the condition of the rule.

The notifications 280 may be generated as a result of triggering rules within the rule implementation system 220 in association with the complex event handler 210. When events match the patterns of a rule condition within the rule implementation system 220, that rule may be triggered generating an action such as a notification 280. The action may include the generation of, or cause the generation of, a new event. The complex event handler 210 may itself process that new event, which may include storing the event in the event log 230 and/or trigger rules within the rule implementation system 220 that match the new event. The actions may also impact or instruct operations of one or more other systems.

An alarm 250 may generally be events related to patients 110 that can be triggered by various medical devices 120. Examples of events can be that lab work has completed, patient or personnel changes have occurred, timers have activated, medical devices 120 have malfunctioned, power outages have occurred, or medical devices 120 have signaled a significant change in vital signs of a patient 110.

A domain specific language 270 may be specified for use within a particular knowledge domain. Example of knowledge domains in a healthcare context may include pharmacy, nursing, radiology, cardiology, and so forth. The domain specific language 270 may be used in conjunction with one or more of the domain modules 260 to support specifying rules for use within the rule implementation system 220. Domain users and/or domain experts may provide rules expressed using their respective domain specific language 270. The rules may be provided in plain text, speech-to-text, or some other format. The rules may also be provided through a graphical user interface, wherein the rules may be constructed using elements of the DSL 270.

The domain module 260 can support inputs using the domain specific language 270 for defining rules within the rule implementation system 220. Each given domain can be given a custom domain specific language 270. Because the domain specific language 270 can be user friendly to domain user, and generally quite specific that given domain, the domain experts generally do not need to be familiar with operational details of the complex event handler 210 or the rule implementation system 220. A condition generator functionality associated with the domain module 260 may process inputs expressed in the domain specific language 270 into a format for insertion as a rule into the rule implementation system 220. Similarly, an action generator functionality associated with the domain module 260 may process inputs expressed in the domain specific language 270 to extract resultant actions associated with the rule being triggered within the rule implementation system 220.

The complex event handler 210, the rule implementation system 220, systems associated with the alarms 250, systems associated with the domain module 260, systems associated with the notifications 280, or any other systems associated with the technology presented herein may be any type of computing machine such as, but not limited to, those discussed in more detail with respect to FIG. 5. Furthermore, any modules (such as the complex event handler module 240, or domain module 260) associated with any of these computing machines or any other modules (scripts, web content, software, firmware, or hardware) associated with the technology presented herein may by any of the modules discussed in more detail with respect to FIG. 5. The computing machines discussed herein may communicate with one another as well as other computer machines or communication systems over one or more networks such as network 190. The network 190 may include any type of data or communications network including any of the network technology discussed with respect to FIG. 5.

Figure 3:
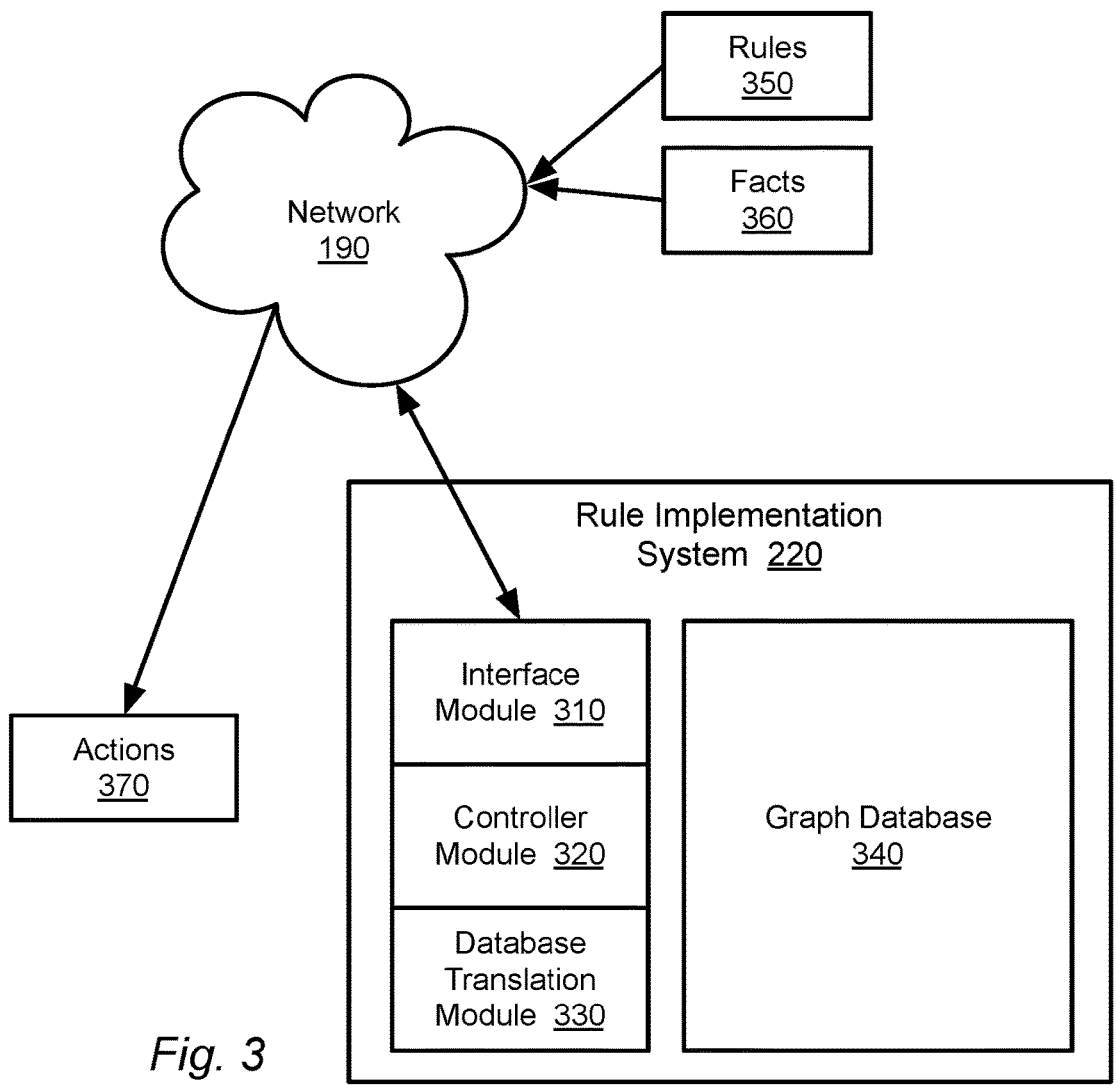
FIG. 3 is a block diagram depicting a rule implementation system associated with a graph database in accordance with one or more embodiments presented herein.

FIG. 3 is a block diagram depicting a rule implementation system 220 associated with a graph database 340 in accordance with one or more embodiments presented herein. This example rule implementation system 220 can operate within the complex event handler 210 to match incoming and prior events to trigger various actions 370 such as notifications 280. The rule implementation system 220 can operate on rules 350 and facts 360 to establish additional rules 350, additional facts 360, or trigger actions 370 such as notifications 280. It should be appreciated that in this context, the facts 360 may be incoming and prior events associated with the complex event handler 210. The rule implementation system 220 can include various modules such as an interface module 310, a controller module 320, and a database translation module 330. The rule implementation system 220 can operate directly within, or in conjunction with, a graph database 340. Rules 350, facts 360, or actions 370 associated with the rule implementation system 220 may be communicated directly to or from the rule implementation system 220. These communications may also occur in conjunction with one or more networks 190.

A rule 350 associated with the rule implementation system 220 generally consists of two components: a condition and a result. The condition and result of a rule 350 may be said to have an "if, then" relationship. If the condition obtains, then the rule 350 is triggered causing the result to be fired. The condition generally obtains by the existence, or truth, of one or more facts 360. For example, a condition could be, "if it is Wednesday," which would trigger when presented with the fact that the day of the week is Wednesday. The result of firing a rule 350 generally involves one or more other facts 360 or the generation of an action 370. Firing of the rule 350 can assert or retract one or more other facts 360. Firing of the rule 350 can also generate one or more actions 370 as output of the rule implementation system 220. Asserting or retracting one or more facts 360 can alter the state of the rule implementation system 220, which may then affect the conditions of other rules 350 causing them to fire. Altering the state of the rule implementation system 220 may also affect the responses rule condition matches processed by the rule implementation system 220.

The graph database 340 can provide the working memory of the rule implementation system 220. This working memory can store information comprising the current state or knowledge of the rule implementation system 220. The graph database 340 can store information in a graph structure where nodes are interconnected by edges. The nodes generally represent entities or things such as individuals, departments, or equipment. Edges generally connect nodes representing the relationship between them. Each node may be associated with one or more properties, which may contain information pertinent to that respective node.

The interface module 310 of the rule implementation system 220 can provide an application programming interface (API), scripting interface, domain-specific language (DSL) 270, or other mechanism for interfacing to the rule implementation system 220. The interface module 310 may support transactions with other modules, systems, or entities associated with the rule implementation system 220. These transactions may involve providing rules 350 or facts 360 to the rule implementation system 220, receiving and reacting to queries or rule condition matches, retrieving rules 350 or facts 360 from the rule implementation system 220, or receiving actions 370 or information associated with actions 370 from the rule implementation system 220.

The controller module 320 of the rule implementation system 220 can process control operations of the rule implementation system 220. Examples of the operations may include executing queries, starting/stopping rule evaluation, and so forth.

The database translation module 330 of the rule implementation system 220 can provide low-level interactions with the graph database 340. These interactions may include performing queries, handling fact node assertion or retraction, database administrative tasks, and so forth.

It should be appreciated that in addition to the interface module 310, controller module 320, database translation module 330, and graph database 340, the rule implementation system 220 may include or interface with other modules. It should also be appreciated that any two or more of these modules may be combined into the same module or modules. Furthermore, any one or more of these modules may split functionally, or load share, between two or more modules or execute on two or more computing machines. Any such modules may operate in a parallel, distributed, or networked fashion without departing from the spirit or scope of the technology presented herein.

Within the rule implementation system 220, a rule-fact graph may be a graph stored in the graph database 340. The rule-fact graph can include various nodes connected by edges. The rule-fact graph within the graph database 340 can serve as the working memory of the rule implementation system 220. This working memory can store information comprising the current state or knowledge of the rule implementation system 220. This information can include various facts 360, which may be stored as nodes connected by edges representing relationships between the nodes such that the nodes and edges together can encode the rules 350.

Within the rule implementation system 220, rule interpretation may be provided by executing queries on the rule-fact graph within the graph database 340. The queries may be associated with inputs posed to the rule implementation system 220 to be matched against rule conditions. These may relate to incoming and prior events. The queries can pattern-match facts 360 against the encoded rules 350 determining which of the rules 350 to apply. The condition portion of each rule 350 may be tested against the current state of the working memory by pattern matching against the rule-fact graph. The consequent results can update the knowledge represented by the rule-fact graph by asserting or retracting information. The consequent results can also update the event knowledge by generating an event that will in turn be stored to the event log 230. Rule interpretation can execute forward chaining when updated information affects other rules 350 implied within the rule-fact graph. The results consequent to the condition can also trigger actions 370 which may include generating new events. Queries of the rule-fact graph within the graph database 340 can leverage a schema-free storage structure supporting index-free adjacency where any node may be directly linked (by one or more edges) to its adjacent nodes such that index lookups are unnecessary.

Within the rule implementation system 220, representing rules 350 within the graph database 340 provides the ability to establish adjacencies between any nodes (and thus relationships between facts 360) without having to rebuild schemas or introduce associating tags or indices. Accordingly, rules 350 may be changed or introduced anew within the rule-fact graph very efficiently and with reduced effort or overhead. Changing this rule representation in a traditional database for a huge number of entries can be extremely time consuming and nearly impossible, if such rules changed as frequently as they might in certain complex enterprise environments such as health care information systems.

Some example benefits to the rule implementation system 220 leveraging the graph database 340 relate to it being more suitable for managing ad hoc and changing data with evolving schemas. For example, in a healthcare enterprise such as a hospital department, the number of nurses may vary from shift to shift, as might the number of patients. Furthermore, the roles of the nurses may change and the assignments relating the nurses to specific patients may also change. When additional facts 360 and rules 350 associated with the hospital department come into play, the rule-fact graph can quickly become very large even while being dynamic (rapidly changing). For example, the additional events, facts 360, and rules 350 may relate to procedures, medications, food service, radiology, tests, specialist referrals, admit/discharges, code emergencies, monitoring alarms, and so forth. Other example additional events, facts 360, and rules 350 may relate to routing messages, alarms, notifications, voice calls, text messages, or other communication modalities to one or more nurses (or wireless mobile devices associated therewith) within a healthcare enterprise. This type of information is also well addressed by the schema-less structure support of the rule implementation system 220 and its associated graph database 340.

Another example benefit to the rule implementation system 220 leveraging the graph database 340 stems from the native pattern matching capabilities of the graph database 340. Such native pattern matching support can provide for significant increases in efficiencies related to rule interpretation and associated queries.

Yet another example benefit to the rule implementation system 220 leveraging the graph database 340 relates to the disk-backed performance of the rule implementation system 220 and its associated graph database 340. Disk-backed operation can provide persistence of state by maintain information within the graph database 340. Disk-backed operation can also overcome working memory limitations encountered in operating on a rule-fact graph of ever increasing size and complexity. It should be appreciated that this "working knowledge" associated with the rule-fact graph maintains rules and is in contrast to the prior event knowledge stored in the event log 230.

The rule implementation system 220, systems associated with the rules 350, facts 360, actions 370, or any other systems associated with the technology presented herein may be any type of computing machine such as, but not limited to, those discussed in more detail with respect to FIG. 5. Furthermore, any modules (such as the interface module 310, controller module 320, or database translation module 330) associated with any of these computing machines or any other modules (scripts, web content, software, firmware, or hardware) associated with the technology presented herein may by any of the modules discussed in more detail with respect to FIG. 5. The computing machines discussed herein may communicate with one another as well as other computer machines or communication systems over one or more networks such as network 190. The network 190 may include any type of data or communications network including any of the network technology discussed with respect to FIG. 5.

Example Processes

According to methods and blocks described in the embodiments presented herein, and, in alternative embodiments, certain blocks can be performed in a different order, in parallel with one another, omitted entirely, and/or combined between different example methods, and/or certain additional blocks can be performed, without departing from the scope and spirit of the invention. Accordingly, such alternative embodiments are included in the invention described herein.

Figure 4:
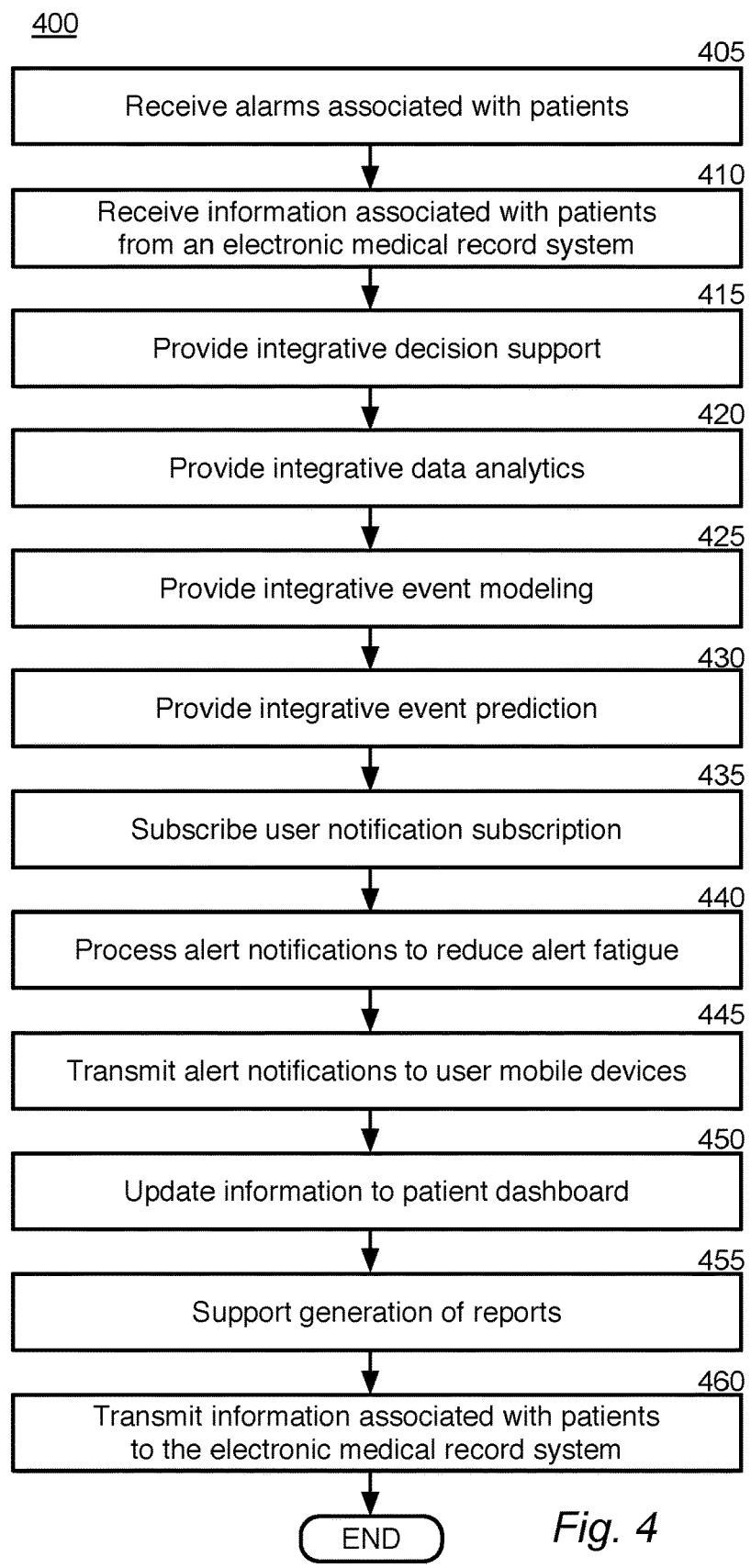
FIG. 4 is a block flow diagram depicting a method for integration and presentation management for mobile healthcare patient information in accordance with one or more embodiments presented herein.

FIG. 4 is a block flow diagram depicting a method 400 for integration and presentation management for mobile healthcare patient information in accordance with one or more embodiments presented herein. In block 405, the integration management system 130 can receive alarm indications associated with one or more patients 110. Alarms generated by the patient 110 or by associated medical devices 120 may be relayed to the integration management system 130 as they occur. The integration management system 130 can generate intelligent alarms by evaluating, aggregating, and/or processing alarm or alert conditions it receives and determining the proper resultant alarm signals to communicate to the clinical users. Furthermore, the integration management system 130 can process multiple alarms and/or incorporate multiple sources of other information to generate multivariate alarms. For example, an alarm from a patient monitor may be evaluated along with additional patient information from electronic medical records 140 or patient physiological information from one or more medical devices to generate a multivariate alarm. Also, the integration management system 130 can apply models, statistical data, and information trends to predict future alarms. For example, various physiological data samples along with information about a recent invasive surgery may support the generation of a predictive alarm indicating that a patient may be entering a state of sepsis.

In block 410, the integration management system 130 can receive information associated with patients 110 from the electronic medical records 140. This information may include previous collected data about a current patient 110 or comparative data collected over a set of prior patients 110. According to certain examples, information about the patient 110 associated with an alarm or alert may be retrieved from the electronic medical records 140. According to various examples, information from current or past patients may be retrieved from the electronic medical records 140 regarding age, gender, alarms generated, medications, procedures, medical monitoring waveforms, medical imaging, current images, current video, voice intercom, health conditions (e.g. cancer, cardiac, diabetic, dementia, etc.), and so forth.

In block 415, the integration management system 130 can process events, such as alarms or alerts, and present resultant notifications or other information to appropriate clinical care providers within a healthcare environment. The integration management system 130 may use rule implementation systems, event handlers, or other machine intelligence mechanisms. For example, the decision module 132 can apply rules to presentation of notifications. Application of the decision module 132 may leverage various facts or other parameters. These may include information related to the received alarm, context of the clinical users (for example, locations, skills, roles, etc.), context of the patient (for example, from the electronic medical records 140), relationships between the patient 110 and the clinical users, and so forth.

In block 420, the integration management system 130 can leverage integrative data analytics techniques to process data associated with alarms, alerts, patients 110, electronic medical records 140, use mobile devices 150, and various other sources. The data analysis module 134 associated with the integration management system 130 may support the various data analytic operations. Integrative data analytics techniques can combine data from multiple sources and domains into any data analysis processes.

In block 425, the integration management system 130 can leverage integrative event modeling techniques to generate predictive and analytical data-driven models associated with alarms, alerts, notifications, patients 110, electronic medical records 140, and other clinical information and communication systems. The modeling module 136 associated with the integration management system 130 can support these operations. Event modeling algorithms operable to combine data, information, and events from multiple sources and domains into statistical models may be leveraged to explain and/or predict clinical events and associated alarms and/or notifications through various contexts. The processing of the data analysis module 134 can be used to create models for patient data for current and future analyses of symptoms that are related to patients 110. The modeling module 136 can also be used to supply information to the integration management system 130 in association with user mobile devices 150 as to how to react to various alarm contexts from medical devices 120.

In block 430, the prediction module 138 can predict types and characteristics of notifications or other presentations. These predictions may be based on probability or likeliness of future events. Data stores of contextual information can support predictions of various outcomes in view of incoming data through mechanisms of statistical analysis, previous behaviors, or previous actions of objects or people. Data from electronic medical records 140, patients, medical devices, and other diverse clinical information sources may be intelligently integrated to drive predictive algorithms.

In block 435, the user mobile devices 150 may interface with the integration management system 130 to allow clinicians to use subscription services to subscribe only to events within their skill sets, physical location or proximity to patients 110, or mere availability at the health care facility at specific times.

In block 440, the integration management system 130 may process alert notifications by subscription levels in order to reduce alert fatigue to caregivers. By allowing alerts to be triggered to user mobile devices 150 and patient dashboards 160 based on these pre-defined criteria, alert fatigue can be greatly reduced. This reduction in alert fatigue can improve health care worker productivity based on pre-defined roles and other criteria. By receiving only subscribed alerts, a caregiver can be more attentive to their specific role.

The integration management system 130 can apply rules for presenting the alarm to the user. The alarm can be routed to a user. Whether the alarm gets routed, to whom it get routed, and how it is to be presented (for example, so as to avoid alarm fatigue) may all be determined by applying the rules 350. The rules 350 may be applied according to the rule implementation system 220 associated with the integration management system 130. Application of the rules 350 may use as facts 360, other parameters, various information related to the received alarm, the user context, the patient context, and the relationship between the patient 110 and the user, and/or various other context information. Application of rules 350, modeling, analytics, and other techniques presented herein can reduce alarm fatigue, alter fatigue, and notification fatigue.

In block 445, alert notifications can be transmitted by the integration management system 130 to user mobile devices 150. The alert notifications may be filtered such that only subscribed alert notifications are delivered. The integration management system 130 may use various modules to present alert notifications to caregivers. The user devices 150 may include smart phones, tablets, or desktop computers, for example. The alerts given by user mobile devices can be presented as sounds or alarm tones played on the user mobile device 150. Alarms may also be presented as vibrations, flashing lights, graphical display, textual displays, animations, or any combination thereof.

In block 450, patient information can be updated by the integration management system 130 to display on patient dashboards 160. The patient dashboard 160 may be a presentation device associated with the medical devices 120 and may be physically represented as a display monitor, smartphone, tablet, or any other device capable of displaying visual and/or audible data to staff in a clinical environment.

The patient dashboard 160 may provide real-time viewable statuses of patients 110. The status may include vital signs such as heart rate, blood pressure, or blood sugar levels, for example. Such visual representation may support reduction in alarm fatigue, alert fatigue, and notification fatigue in caregivers by allowing a the caregiver to quickly view particular statuses of the patient 110, rather than being required to respond to more frequent interruptions form alerts, alarms, and/or notifications.

In block 455, reports 170 can be generated by the integration management system 130 as presentations associated with the status of the patient 110. These may be electronic and viewable on various devices such as user mobile devices 150, including smart phones, tablets, or desktop computers, for example.

In block 460, information associated with patients 110 can be transmitted to the electronic medical record system 140 by the integration management system 130. This transmission of data can update the electronic medical records 140 of a patient 110 at regular intervals to keep track of any changes associated with the patient 110. The integration management system 130 may also receive alerts from the electronic medical records 140 if the patient presents symptoms that are actionable.

Example Systems

FIG. 5 depicts a computing machine 2000 and a module 2050 in accordance with one or more embodiments presented herein. The computing machine 2000 may correspond to any of the various computers, servers, mobile devices, embedded systems, or computing systems presented herein. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a vehicular information system, one more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations and functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain embodiments, the processor 2010 along with other components of the computing machine 2000 may be a virtualized computing machine executing within one or more other computing machines.

The system memory 2030 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 2030 also may include volatile memories, such as random access memory ("RAM"), static random access memory ("SRAM"), dynamic random access memory ("DRAM"), and synchronous dynamic random access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device such as the storage media 2040.

The storage media 2040 may include a hard disk, a floppy disk, a compact disc read only memory ("CD-ROM"), a digital versatile disc ("DVD"), a Blu-ray disc, a magnetic tape, a flash memory, other non-volatile memory device, a solid sate drive ("SSD"), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for operably coupling the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attachment ("ATA"), serial ATA ("SATA"), universal serial bus ("USB"), Thunderbolt, FireWire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, biometric readers, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks ("WAN"), local area networks ("LAN"), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or an analog communication media such as fiber optic cables, free-space optics, waveguides, electrical conductors, wireless links, antennas, radio-frequency communications, and so forth.

The processor 2010 may be connected to the other elements of the computing machine 2000 or the various peripherals discussed herein through the system bus 2020. It should be appreciated that the system bus 2020 may be within the processor 2010, outside the processor 2010, or both. According to some embodiments, any of the processor 2010, the other elements of the computing machine 2000, or the various peripherals discussed herein may be integrated into a single device such as a system on chip ("SOC"), system on package ("SOP"), or ASIC device.

In situations in which the systems discussed here collect personal information about users, or may make use of personal information, the users may be provided with a opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

One or more aspects of embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the invention should not be construed as limited to any one set of computer program instructions. Further, a skilled programmer would be able to write such a computer program to implement an embodiment of the disclosed invention based on the appended flow charts and associated description in the application text. Therefore, disclosure of a particular set of program code instructions is not considered necessary for an adequate understanding of how to make and use the invention. Further, those skilled in the art will appreciate that one or more aspects of the invention described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described previously. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays ("FPGA"), etc.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of embodiments of the invention. Accordingly, such alternative embodiments are included in the inventions described herein.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of the invention defined in the following claims, the scope of which is to be accorded the broadest interpretation so as to encompass such modifications and equivalent structures.

What is claimed is:

1. A computer-implemented method for managing clinical alerts presented to clinical care users, comprising:
    maintaining, in association with an integration management system, models of clinical alert events in the context of behaviors associated with one or more clinical care users;
    maintaining, in association with the integration management system, models of clinical alert events in the context of a patient;
    receiving, at the integration management system, an alarm indication from a medical device associated with the patient;
    receiving, at the integration management system, patient context information associated with the patient;
    receiving, at the integration management system, information associated with the patient from an electronic medical record system;
    performing, by the integration management system, integrated decision processing, wherein the integrated decision processing integrates two or more of the alarm indication, the models of clinical alert events, the patient context information, and the information from the electronic medical record system;
    applying, by the integration management system, the integrated decision processing to determine if a clinical alert is to be generated;
    applying, by the integration management system, the integrated decision processing to determine a target user from among the one or more clinical care users;
    applying, by the integration management system, the integrated decision processing to determine what type of clinical alert should be presented to the target user;
    transmitting, from the integration management system, the determined clinical alert to a mobile device associated with the target user over a digital communications network in response to determining if the clinical alert is to be generated;
    receiving, at the integration management system, a response to the transmitted clinical alert from the mobile device associated with the target user;
    interpreting, at the integration management system, the received response to the transmitted clinical alert; and
    updating, by the integration management system, information associated with the patient into the electronic medical records system based upon the transmitted clinical alert and the response to the transmitted clinical alert.

2. The computer-implemented method of claim 1, wherein the integrated decision processing comprises integrative data analytics.

3. The computer-implemented method of claim 1, wherein the integrated decision processing comprises integrative event prediction.

4. The computer-implemented method of claim 1, wherein the alarm indication is received from a medical device associated with the patient, and the system associated with the target user comprises a mobile computing device.

5. The computer-implemented method of claim 1, wherein the integrated decision processing to determine if the clinical alert is to be generated is operable to reduce alert fatigue.

6. The computer-implemented method of claim 1, further comprising updating information to a patient dashboard.

7. The computer-implemented method of claim 1, wherein integrated decision processing leverages a rule implementation system.

8. The computer-implemented method of claim 1, wherein integrated decision processing comprises application of a complex event handler comprising a rule implementation system and an event log.

9. The computer-implemented method of claim 1, wherein integrated decision processing leverages a rule implementation system comprising a graph database.

10. The computer-implemented method of claim 1, further comprising receiving information associated with one or more categories of patients from the electronic medical record system.

11. A clinical alert generation system, comprising:
    one or more processing units, and one or more processing modules, wherein the clinical alert generation system is configured by the one or more processing modules to:
    maintain models of clinical alert events in the context of behaviors associated with one or more clinical care users;
    maintain models of clinical alert events in the context of a patient;
    receive an alarm indication from a medical device associated with the patient;
    receive patient context information associated with the patient;
    receive information associated with the patient from an electronic medical record system;
    perform integrated decision processing, wherein the integrated decision processing integrates two or more of the alarm indication, the models of clinical alert events, the patient context information, and the information from the electronic medical record system;
    apply the integrated decision processing to determine if a clinical alert is to be generated;
    apply the integrated decision processing to determine a target user from among the one or more clinical care users;
    transmit the clinical alert to a mobile device associated with the target user over a digital communications network in response to determining if the clinical alert is to be generated;
    receive, from the mobile device associated with the target user, a response to the transmitted clinical alert;
    interpret the received response to the transmitted clinical alert; and
    update information associated with the patient into the electronic medical record system based upon the transmitted clinical alert and the response to the transmitted clinical alert.

12. The clinical alert generation system of claim 11, wherein the integrated decision processing comprises integrative data analytics.

13. The clinical alert generation system of claim 11, wherein the integrated decision processing comprises integrative event prediction.

14. The clinical alert generation system of claim 11, wherein the alarm indication is received from a medical device associated with the patient, and the system associated with the target user comprises a mobile computing device.

15. The clinical alert generation system of claim 11, wherein the determining if the clinical alert is to be generated is operable to reduce alert fatigue.

16. The medical alarm management system of claim 11, wherein the clinical alert generation system is further configured by the one or more processing modules to update information to a patient dashboard.

17. The clinical alert generation system of claim 11, wherein integrated decision processing comprises application of a complex event handler comprising a rule implementation system and an event log.

18. The clinical alert generation system of claim 11, wherein integrated decision processing leverages a rule implementation system comprising a graph database.

19. The clinical alert generation system of claim 11, wherein the clinical alert generation system is further configured by the one or more processing modules to receive information associated with one or more categories of patients from the electronic medical record system.

20. A computer program product, comprising:
  a non-transitory computer-readable storage medium having computer-readable program code embodied therein that, when executed by one or more computing devices, perform a method comprising:
  maintaining models of clinical alert events in the context of behaviors associated with one or more clinical care users;
  maintaining models of clinical alert events in the context of a patient;
  receiving an alarm indication from a medical device associated with the patient;
  receiving patient context information associated with the patient;
  receiving information associated with the patient from an electronic medical record system;
  performing integrated decision processing, wherein the integrated decision processing integrates two or more of the alarm indication, the models of clinical alert events, the patient context information, and the information from the electronic medical record system;
  applying the integrated decision processing to determine if a clinical alert is to be generated;
  applying the integrated decision processing to determine a target user from among the one or more clinical care users;
  applying the integrated decision processing to determine what type of clinical alert should be presented to the target user;
  transmitting the determined clinical alert to a mobile device associated with the target user over a digital communications network in response to determining if the clinical alert is to be generated;
  receiving, from the mobile device associated with the target user, a response to the transmitted clinical alert; and
  updating information associated with the patient into the electronic medical records system based upon the transmitted clinical alert and the response to the transmitted clinical alert.

* * * * *